US008357490B2

(12) United States Patent
Froehlich et al.

(10) Patent No.: US 8,357,490 B2
(45) Date of Patent: Jan. 22, 2013

(54) INTEGRATED INSTRUMENT PERFORMING SYNTHESIS AND AMPLIFICATION, AND A SYSTEM AND METHOD THEREOF

(75) Inventors: Thomas Froehlich, Bichl (DE); Martin Gutekunst, Eberfing (DE); Dieter Heindl, Paehl (DE); Angelika Roesler, Sindelsdorf (DE); Rudolf Seibl, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/841,708

(22) Filed: Jul. 22, 2010

(65) Prior Publication Data

US 2011/0177514 A1    Jul. 21, 2011

Related U.S. Application Data

(63) Continuation of application No. PCT/EP2009/000331, filed on Jan. 21, 2009.

(30) Foreign Application Priority Data

Jan. 23, 2008   (EP) .................................. 080012438

(51) Int. Cl.
    *C12Q 1/68*     (2006.01)
    *C12P 19/34*    (2006.01)
    *C40B 60/02*    (2006.01)
    *C40B 60/04*    (2006.01)
    *C40B 60/08*    (2006.01)

(52) U.S. Cl. ......... 435/6.12; 435/6.1; 435/6.11; 506/34; 506/35; 506/37

(58) Field of Classification Search ................ None
    See application file for complete search history.

(56) References Cited

U.S. PATENT DOCUMENTS

| 5,118,801 A | 6/1992 | Lizardi et al. |
| 5,247,081 A | 9/1993 | Edge |
| 5,258,506 A | 11/1993 | Urdea et al. |
| 5,368,823 A | 11/1994 | McGraw et al. |
| 5,514,789 A | 5/1996 | Kempe |
| 5,538,848 A | 7/1996 | Livak et al. |
| 5,541,314 A | 7/1996 | McGraw et al. |
| 5,700,637 A | 12/1997 | Southern |
| 6,174,670 B1 | 1/2001 | Wittwer et al. |
| 2002/0176811 A1 | 11/2002 | Peck et al. |
| 2003/0086829 A1 | 5/2003 | Livesay et al. |
| 2003/0113236 A1 | 6/2003 | Cracauer et al. |
| 2008/0003649 A1 | 1/2008 | Maltezos et al. |

FOREIGN PATENT DOCUMENTS

| DE | 297 20 432 U1 | 11/1997 |
| EP | 0 683 790 B1 | 2/1994 |
| WO | 97/46707 | 12/1997 |
| WO | 97/46712 | 12/1997 |
| WO | 97/46714 | 12/1997 |
| WO | 2007/082713 A1 | 7/2007 |

OTHER PUBLICATIONS

Jefferies et al., "Automated Pneumococcal MLST Using Liquid-Handling Robotics and a Capillary DNA Sequencer," Molecular Biotechnology, 2003, vol. 24, pp. 303-307.*
Anderson, Emma et al., Novel Photocleavable Universal Support for Oligonucleotide Synthesis, 2003, vol. 22, Nos. 5-8, pp. 1403-1406, UK.
Beaucage, Serge, Oligodeoxyribonucleotides Synthesis, Phosphoramidite Approach, Methods in Molecular Biology 20, 1993, pp. 33-61, USA.
Bernard, et al., Integrated Amplification and Detection of the C677T Point Mutation in the Methylenetetrahydrofolate Reductase Gene by Fluorescence Resonance Energy Transfer and Probe Melting Curves, Anal. Biochem, 1998, pp. 101-107, USA.
Gait, M.J., Oligonucleotide Synthesis—A Practical Approach, IRL Press, 1984, pp. 1-2, Oxford.
Gilar, et al., Purification of Crude DNA Oligonucleotides by Solid-Phase Extraction and Reversed-Phase High Performance Liquid Chromatography, Journal of Chromatography, 890, 2000, pp. 167-177, USA.
Gildea, et al., A Versatile Acid-Labile Linker for Modification of Synthetic Biomolecules, Tetrahedron Letters, vol. 31, No. 49, pp. 7095-7098, 1990, Great Britain.
Higuchi, et al., Simultaneous Amplification and Detection of Specific DNA Sequences, Bio/Technology, vol. 10, 1992, pp. 413-417, USA.
Higuchi, et al., Kinetic PCR Analysis: Real-Time Monitoring of DNA Amplification Reactions, Bio/Technology vol. 11, Sep. 1993, pp. 1026-1030, USA.
Matthews, et al., Analytical Strategies for the Use of DNA Probes, Analytical Biochemistry, vol. 169, 1988, pp. 1-25, USA.
McMinn, et al., An Orthogonal Solid Phase Support for the Synthesis of Oligonucleotides Containing 3'-Phosphates and Its Application in the Preparation of Photolabile Hybridization Probes, Tetrahedron Letters, vol. 39, 1998, pp. 4155-4158, USA.
Pon, et al., Tandem Oligonucleotide Synthesis Using Linker Phosphoramidites, Nucleic Acids Research, vol. 33, No. 6., 2005, pp. 1940-1948, U.K.
Rayner, et al., MerMade: An Oligodeoxyribonucleotide Synthesizer for High Throughput Oligonucleotide Production in Dual 96-Well Plates, Genome Research, vol. 8, No. 7, 1998, pp. 741-747, USA.
Cheng, et al., High Throughput Parallel Synthesis of Oligonucleotides with 1536 Channel Synthesizer, Nucleic Acids Research, vol. 30, No. 18, 2002, pp. 1-7, China.
International Search Report, Appl. No. PCT/EP2009/000331, filed Jan. 21, 2009, Search Report completed Jul. 9, 2009, pp. 1-7.
Written Opinion of the International Search Report, Appl. No. PCT/EP2009/000331, filed Jan. 21, 2009, pp. 1-7.

* cited by examiner

Primary Examiner — Young J Kim
(74) Attorney, Agent, or Firm — Roche Diagnostics Operations, Inc.

(57) ABSTRACT

An integrated instrument for oligonucleotide synthesis and PCR, and a system and method thereof are disclosed. The integrated instrument is basically composed of two independent modules. The first module is a unit for chemical de novo synthesis of oligonucleotides such as oligonucleotide primers and/or oligonucleotide hybridization probes. The second module is a unit for performing an analytical polymerase chain reaction amplification in real time, i.e. a qPCR. The two modules are operatively linked to each other in such a way that a user can load a nucleic sample to be analyzed into the integrated instrument and perform a PCR reaction by programming the instrument without a previous external synthesis of oligonucleotide amplification primers.

19 Claims, 3 Drawing Sheets

INTEGRATED INSTRUMENT PERFORMING SYNTHESIS AND AMPLIFICATION, AND A SYSTEM AND METHOD THEREOF

TECHNICAL FIELD

The present disclosure relates to the field of nucleic acid chemistry and analysis, and in particular, to an integrated instrument for the de novo oligonucleotide primer and probe synthesis and subsequent amplification of a target nucleic acid to be analyzed, and a system and method thereof.

BACKGROUND

Amplification of DNA by polymerase chain reaction (PCR) is a technique fundamental to molecular biology. Nucleic acid analysis by PCR requires sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. Sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR. See, for example, U.S. Pat. No. 6,174,670.

Monitoring fluorescence during each cycle of PCR initially involved the use of ethidium bromide. (Higuchi, R., Dollinger, G., Walsh, P S, and Griffith, R., Simultaneous amplification and detection of specific DNA sequences, Bio/Technology 10 (1992) 413-417; Higuchi, R., Fockler, C., Dollinger, G., and Watson, R., Kinetic PCR analysis: real time monitoring of DNA amplification reactions, Bio/Technology 11 (1993) 1026-1030). In that system fluorescence is measured once per cycle as a relative measure of product concentration. Ethidium bromide detects double stranded DNA; if template is present fluorescence intensity increases with temperature cycling. Furthermore, the cycle number where an increase in fluorescence is first detected increases inversely proportionally to the log of the initial template concentration. Other fluorescent systems have been developed that are capable of providing additional data concerning the nucleic acid concentration and sequence.

In kinetic real time PCR, the formation of PCR products is monitored in each cycle of the PCR. The amplification is usually measured in thermocyclers which have additional devices for measuring fluorescence signals during the amplification reaction.

A prerequisite for the performance of real time PCR is the availability of synthetic oligonucleotides which can act as amplification primers and as hybridization probes. Synthetic (deoxy)-oligonucleotides are usually prepared on a solid phase with the aid of phosphoramidite chemistry. Glass beads having pores of a defined size (abbreviated in the following as CPG=controlled pore glass) are usually used as the solid phase. The first monomer is bound to the support via a cleavable group such that the oligonucleotide can be cleaved after the solid phase synthesis is completed. The first monomer additionally contains a transiently protected hydroxyl group, whereas dimethoxytrityl (DMT) being usually used as the protective group. The protective group can be removed by acid treatment. Then 3'-phosphoramidite derivatives of (deoxy)-ribonucleosides that are also provided with a DMT protective group are then coupled in a cyclic process to each successive reactive group after is has been freed of the DMT protective group. The monomers contain additional permanent protecting groups, i.e. OH protecting groups and base protecting groups which are cleaved after the synthesis is completed. For review, see: Oligonucleotide synthesis: a practical approach. Ed. M. J. Gait, IRL Press Oxford, 1988.

Oligonucleotide synthesizers for high throughput oligonucleotide synthesis are commercially available. "Dr Oligo" (BiolyticLab Performance Inc), "Mermade" (Bioautomation) and "Polyplex" (Genmachines Genomic Solutions Inc) are synthesizer using microtiterplates with a frit in each bottom of a well as synthesis platform. The frit retains the solid support inside the well. Alternatively a 96 position rack is used in which in each position fits a synthesis column (commercially available from Applid Biosystems) such columns contain two frits one at the bottom and the other on the top of the solid support. Alternatively, CPG Frits could be used (available from CTGen)

Such Synthesizers are described in U.S. Pat. No. 5,368,823; U.S. Pat. No. 5,541,314; EP 0 683 790; US 2003/113,236; US 2003/086,829; US 2002/176,811 and Rayner, Simon, et al., Genome Research 8(7) (1998); Peck, Konan, Nucleic Acids Res. 30 (2002) 18 e93

However, there is no integrated system available which enables for an automated PCR reaction, which includes synthesis of the required oligonucleotides.

SUMMARY

In one embodiment, an integrated instrument is disclosed and comprises an oligonucleotide synthesizer unit S; and a real time PCR thermocycler unit P, whereas unit S and unit P are operatively linked to each other.

In another embodiment, a system is disclosed and comprises an instrument as disclosed above; and at least one solid support disposable which is capable of acting as a starting support for oligonucleotide synthesis.

In still another embodiment, a method of performing a real time PCR is disclosed and comprises (i) performing an oligonucleotide synthesis of a first primer and a second primer in an integrated instrument as disclosed above; (ii) adding into a reaction vessel located in the integrated instrument a) the nucleic acids sample to be analyzed, b) the first and second primer synthesized in step (i), and c) all other reagents necessary for a real time PCR of the target nucleic acid; and (iii) amplifying and simultaneously monitoring amplification of the target DNA in the integrated instrument.

BRIEF DESCRIPTION OF THE DRAWINGS

The following figures and example are provided to aid the understanding of the present invention, the true scope of which is set forth in the appended claims. It is understood that modifications can be made in the procedures set forth without departing from the spirit of the invention.

DETAILED DESCRIPTION

Instrument and System

An embodiment the present invention is directed to an integrated instrument comprising
- an oligonucleotide synthesizer unit S, and
- a real time PCR thermocycler unit P, whereas unit S and unit P are operatively linked to each other.

The operative linkage can be an interface unit I, the interface being capable of handling oligonucleotides synthesized by the unit S in such a way that they can be used as primers and facultatively as probes in the unit P.

The unit S can comprise means for holding at least one CPG column or an array of CPG columns, whereas the array of CPG columns is preferably in a microtiter plate format. Alternatively, the unit S comprises means for holding a planar support for oligonucleotide synthesis.

In case the unit S comprises means for holding at least one CPG column or an array of CPG columns, the unit S may also comprise a suction device, which is capable of generating underpressure in order to remove liquid from at least one column or reaction vessel or a multitude of columns or a cavity or a multitude of cavities through a frit. The unit S may further comprise means for holding a disposable with at least one cavity which is preferably a multi cavity disposable and most preferably a microtiter plate or picotiter plate.

In addition, the unit S may further comprise a sealing device which is capable of sealing the one or more cavities of the multi-cavity disposable. Furthermore, the unit S further may comprise means for holding at least one reversed phase column or an array of reversed phase columns. Alternatively, the one or more cavities of the multi cavity disposable have a surface coated with a compound capable of capturing a synthesized oligonucleotide.

Finally, the unit S further may comprise means for illumination of oligonucleotides adapted to induce cleavage of a photolabile chemical bonding.

The unit I may comprise a pipetting robot. The unit I may also comprise a UV measurement device. The unit I may further comprise a storage means for storing a plurality of multi-cavity disposables, which are preferably microtiter plates or picotiter plates. In addition, the unit I may comprise means for preparing at least a first PCR reaction mixture. Preferably, the unit I further then comprises a transport means for transporting the PCR reaction mixtures into unit P.

Another embodiment of the present invention also provides a system comprising
- an instrument as disclosed herein in its multiple variations, and
- at least one solid support disposable which is capable of acting as a starting support for oligonucleotide synthesis as disclosed herein in its multiple variations.

For example, the system may specifically comprise
- a unit S with means for holding at least one CPG column or an array of CPG columns, whereas the array of CPG columns is preferably in a microtiter plate format, means for holding a disposable with at least one cavity which is preferably a multi cavity disposable and most preferably a microtiter plate or picotiter plate, and
- a solid support disposable which comprises at least one column with a frit comprising CPG particles.

In a further embodiment, such a system further comprises
- a unit I with a storage means for storing a plurality of multi-cavity disposables, which are preferably microtiter plates or picotiter plates, and
- a plurality of multi-cavity disposables, which are preferably microtiter plates or picotiter plates.

Other embodiments of the present invention also provide methods for performing a real time PCR. One such method comprises
(i) performing an oligonucleotide synthesis of a first primer and a second primer in an integrated instrument,
(ii) adding into a reaction vessel located in the integrated instrument
   a. the nucleic acids sample to be analyzed,
   b. the first and second primer synthesized in step (i), and
   c. all other reagents necessary for a real time PCR of the target nucleic acid, and
(iii) amplifying and simultaneously monitoring amplification of the target DNA in the integrated instrument.

Prior to step (ii), the UV absorbance of the synthesized primers can be monitored, preferably in a flow through cuvette. For reasons of quality control, it is also possible to perform an oligonucleotide test synthesis in a representative number of reaction sites and to test the generated test oligonucleotides subsequently tested for their ability to act as primers in a predefined PCR amplification reaction.

Furthermore, subsequent to step (i) it is possible to store the primers in a multi cavity disposable. In some instances this can be done for 24 hours or even longer, in particular, if the multi cavity disposable is placed in a temperature controlled holding means. Thus, it is possible to perform step (i) exactly once and to perform steps (ii) and (iii) multiple times in different multi cavity disposables.

Preferably, the primers of step (i) are synthesized on a CPG solid support. Alternatively, the solid support may be an arrayed solid support. It is also within the scope of the present invention if two different primers are synthesized on the same CPG solid support or the same spot of an arrayed planar solid support, if each primer is synthesized with a different set of phosphoramidites with each set having a different 5' protective group. Preferably, the different protective groups are photocleavable at different wavelengths. Alternatively one transient protecting group is acid labile and the other protecting group is photolabile. Furthermore, two oligonucleotides could be synthesized in one cavity respectively at one location by using standard DMT protection and a cleavable linker which is introduced during oligonucleotide synthesis and which is located in between both oligonucleotides. Tandem oligonucleotide synthesis using linker phosphoramidites (Pon, Richard Shuyuan, T., Yu, Nucleic Acids Research 33(6) (2005) 1940-1948).

In other embodiments of the present invention, specific methods for oligonucleotide synthesis on a CPG solid support are provided, which are extremely useful for instruments and systems disclosed in this application. In one embodiment, the synthesized primers are subsequently purified via a reversed phase chromatography. In another embodiment, the primers are synthesized with a 5' hapten modification. Subsequent to the synthesis, the primers are captured by a solid support which is coated with a hapten binding moiety.

In a further embodiment, the newly synthesized primers are coupled to the CPG-solid support via a photocleavable linker and the primers are cleavable from the CPG-solid support by means of illumination. If synthesized in the standard 3'-5' direction after photocleavage the 3' end of the oligonucleotide is phosphorylated. The phosphate group could be enzymatically cleaved during PCR In a still further embodiment, primers comprising photocleavable linkers are synthesized on the surface of an arrayed planar solid support, and subsequent to the synthesis cleaved from the solid support into a first multi-cavity disposable by means of illumination.

A preferred embodiment of the present invention is directed to an integrated instrument for oligonucleotide synthesis and a subsequent enzyme mediated primer extension reaction such as PCR. The integrated instrument is basically composed of two independent modules which are operatively linked to each other. The first module is a unit for the chemical de novo synthesis of oligonucleotides such as oligonucleotide primers and/or oligonucleotide hybridization probes. The second module is a unit for performing a primer extension reaction such as NASBA or rolling circle amplification or in particular an analytical polymerase chain reaction amplification in real time, i.e. a qPCR or real time PCR. Such a PCR device comprises a thermocycler unit, which is preferably a temperature controllable thermoblock, and a detection unit such as a CCD camera.

The two modules are operatively linked to each other in such a way that a user can load a nucleic sample that shall be analyzed into the inventive instrument and perform a PCR reaction without a previous external synthesis of oligonucleotide amplification primers by just programming the instrument. Thus, subsequent to oligonucleotide synthesis, the oligonucleotides are automatically handled in such a way that without intermediate opening of the instrument the oligonucleotides are directly loaded into reaction vessels, in which after addition of additional other required reagents, a PCR amplification can be performed.

In other words, an instrument according to an embodiment of the present invention comprises
an oligonucleotide synthesizer unit S, and
a real time PCR thermocycler unit P,
whereas unit S and unit P are operatively linked to each other.

The synthesizer unit S may be a synthesizer which is preferably capable of synthesizing multiple oligonucleotides in parallel. The synthesis is done under inert gas such as Argon. Movement of synthesis fluids and purification fluids is achieved by means of Argon pressure or by means of applying a respective vacuum.

Typically, the different reaction compartments for parallel synthesis of oligonucleotides are arranged in a two dimensional array format with equal distances between neighbored reaction compartments. Preferably, such an array format is a format which is compatible with a typical microtiter or picotiter plate format. For example, 24 reaction compartments are arrayed in a 4×6 matrix, 96 reaction compartments are arrayed in a 8×12 matrix, 384 reaction compartments are arrayed in a 16×24 matrix or 1536 reaction compartments are arrayed in a 32×48 matrix.

Usually, all units of such an integrated instrument are placed within one housing. Thus, the risk of contamination, which might result in the generation, and detection of unspecific PCR amplification products is rather low.

An instrument according to the present invention usually comprises an interface unit I, which operatively connects the synthesizer unit S and the real time PCR unit P. Such an interface is capable of handling oligonucleotides synthesized by the unit S in such a way that they can be used as primers and facultatively as probes in the unit P. The interface is designed in such a way that after appropriate user programming, PCR amplification primers and facultatively also detection probes are synthesized by unit S, subsequently transferred by the interface unit I to a disposable containing a PCR reaction mixture and subsequently, a real time PCR reaction is performed by unit P. Yet, it is also within the scope of the invention that the interface unit I is capable of storing synthesized oligonucleotides and PCR is performed at later on.

Another embodiment of the present invention is directed to an integrated system for oligonucleotide synthesis and a subsequent analytical PCR reaction in real time. More precisely, the system comprises
an instrument as disclosed above, and
at least one solid support disposable which is capable of acting as a starting support for oligonucleotide synthesis.

First Major Embodiment of Unit S

In a first major embodiment, the synthesis unit S comprises means for holding at least one CPG column or an array of CPG columns which is preferably in a microtiter plate format. CPG columns are well known in the art of oligonucleotide synthesis as a solid support on which synthesis based on Phosphoramidite chemistry can be initiated. The addition of Phosphoramidates as well as all other chemical compound required for the oligonucleotide synthesis is performed according to standard means for oligonucleotide synthesis as they are used in the art. (Oligonucleotide synthesis: a practical approach. Gait, Ed., M., J., IRL Press Oxford, 1984). Base specific supports or universal supports for high throughput synthesis and phosphoramidites are commercially available from different sources. Preferably, mild chemistries are used and most preferred, the tert-butylphenoxyacetyl (t-BPA) strategy.

Preferably, the unit S comprises a suction device, which is capable of generating low to moderate pressure differences in order to remove liquid from at least one column or reaction vessel or a multitude of columns or reaction vessels through a frit. An example for such suction devices is a vacuum pump which is connected to the reaction compartments and/or the columns via an appropriate tube system in order to apply moderate under pressure.

Also preferably, the unit S further comprises means for holding a disposable with at least one cavity. Subsequent to the oligonucleotide synthesis and release from the CPG solid phase, the oligonucleotides are drawn through the frit of the CPG column by the suction device into a cavity of the disposable. For parallel synthesis, the disposable is a multi cavity disposable and most preferably a microtiter plate. Advantageously, the bottom of each cavity of the disposable is a frit.

Furthermore, the unit S can comprise a sealing device which is capable of sealing the one or more cavities of the multi-cavity disposable. Preferably, the sealing device is a movable roller for example made of metal, which puts a deformable plastic sheet on top of the disposable in such a way that the cavity is tightly sealed.

In another embodiment, the a system comprises
an instrument according to the first major embodiment of unit S, and
a solid support disposable which comprises at least one column with a frit comprising CPG particles.

Preferably, the solid support disposable comprises an ordered array of multiple columns with a frit comprising CPG. Also preferably, the system comprises a further disposable with at least one cavity, which is preferably a multi cavity disposable and most preferably a microtiter plate, characterized in that each of the cavities has a frit at its bottom.

In a first specific embodiment, the instrument unit S further comprises means for holding at least one reversed phase column or an array of reversed phase columns. Subsequent to the oligonucleotide synthesis, the permanent protective groups are removed and the oligonucleotide is cleaved from the CPG column with aqueous NH3 by means of cleaving a base cleavable linker like succinate. Cleavage can be performed inside the instrument unit S or preferably outside the instrument in an extra deprotection chamber, which is optionally heatable. Alternatively, in a closed chamber gaseous ammonia can be used for deprotection and cleavage (U.S. Pat. No. 5,514,789).

Depending on the application a purification of the generated 5' Dimethoxytrityl protected oligonucleotide is required. The flow through the column as well as the eluation is driven by gravity or by applying pressure.

The oligonucleotide is eluted into a further disposable with at least one cavity. For parallel synthesis, the disposable is a multi cavity disposable and most preferably a microtiter plate. Advantageously, each cavity is constructed as gel filtration unit which allows further purification of the oligonucleotide by means of gel filtration. For example, this might by a Sephadex G25 filtration In another aspect of this specific embodiment, a system comprises
- an instrument according to the first specific embodiment of unit S,
- a first further disposable which is at least one reversed phase column or an array of reversed phase columns, and
- a second further disposable which comprises at least one sample vessel comprising a gel filtration unit or an array of sample vessels, wherein each vessel comprises a gel filtration unit.

For simple applications the purifications and desalting can be avoided and the crude deprotected oligonucleotides are directly used in unit P A second specific embodiment is directed to a workflow characterized in that during oligonucleotide synthesis on the CPG, the oligonucleotide is 5' modified with a Hapten such as Biotin according to standard methods known in the art (Gildea, Brian, D., Coull, James M., Koster, Hubert, Tetrahedron Letters 31(49) (1990) 7095-8).

Consequently, unit S does not require a reversed phase module, but instead has a holding means for holding a multi cavity disposable, wherein the cavities of the disposable have a surface coated with a compound capable of capturing a synthesized oligonucleotide which is labeled with a Hapten. In case of a Biotin label, an appropriate coating material is Streptavidin.

In another aspect of this embodiment, a system comprises
- an instrument according to the first major embodiment of unit S
- a further disposable with at least one cavity which is preferably a multi cavity disposable and most preferably a microtiter plate, characterized in that each cavity is coated with a Hapten affinity binding compound.

Preferably, the Hapten affinity binding compound is Streptavidin.

Second Major Embodiment of Unit S

A second major embodiment is directed to a workflow in which oligonucleotides are synthesized in such a way that they are removable from the CPG material by means of cleaving a photolabile bonding.

Also in this second major embodiment, the synthesis unit S comprises means for holding at least one CPG column or an array of CPG columns which is preferably in a microtiter plate format. CPG columns are well known in the art of oligonucleotide synthesis as a solid support on which synthesis based on Phosphoramidite chemistry can be initiated.

The unit S may also comprise a controllable suction device, which is capable of generating low to moderate pressure differences in order to remove liquid from at least one column or reaction vessel or a multitude of columns or reaction vessels through a frit. An example for such suction devices is a vacuum pump which is connected to the reaction compartments and/or the columns via an appropriate tube system.

In addition, the unit S further comprises means for holding a disposable with at least one cavity. Subsequent to the oligonucleotide synthesis and release from the CPG solid phase, the oligonucleotides are drawn through the frit of the CPG column by the suction device into a cavity of the disposable. For parallel synthesis, the disposable is a multi cavity disposable and most preferably a microtiter plate.

Due to the specific workflow characterized in that synthesized oligonucleotides can be removed from the CPG by means of cleaving a photolabile bonding, the second major embodiment further comprises means for illumination of oligonucleotides in order to induce cleavage of a photolabile chemical bonding. Appropriate means for illumination depend on the type of photolabile bonding and such means are well known in the art. Instead, this embodiment does not require any sealing devices, reversed phase columns, gel filtration devices or coated microtiter plates.

In another embodiment, a system comprises
- an instrument according to the second major embodiment of unit S, and
- a further disposable with at least one cavity which is preferably a multi cavity disposable and most preferably a microtiter plate Third Major Embodiment of Unit S In a third major embodiment, unit S comprises means for holding a planar support for oligonucleotide synthesis. Preferably, the planar support is structured to provide a plurality of spatially separated areas such that a plurality of spatially separated oligonucleotide syntheses can be performed in an arrayed format. In situ oligonucleotide synthesis on such DNA microarrays is an established method which is well known in the art (see e.g. U.S. Pat. No. 5,700,637). The oligonucleotides are released from the array by means of cleaving a photolabile linker which is cleaved with light from a different wavelength than that used for the oligonucleotide synthesis. Thus, unit S further comprises means for illumination of oligonucleotides in order to induce cleavage of a photolabile chemical linker and in order to cleave the photolabile transient 5' protection group (NPPOC, NVOC).

In another aspect of this embodiment, a system comprises
- an instrument according to the first major embodiment of unit S, and
- a solid support disposable which is planar.

The Interface Unit I

A preferred instrument according to an embodiment of the present invention further comprises an interface unit I, the interface unit I being capable of handling oligonucleotides synthesized by the unit S in such a way that they can be used as primers and facultatively as probes in the unit P.

The interface unit I provides an operative link between the unit S and the unit P and usually, all the units are placed within one housing in order to minimize the risk of contamination which might result in the generation and detection of unspecific PCR amplification products.

The interface unit I is designed in such a way that synthesized PCR amplification primers and also facultatively hybridization probes can subsequently be transferred from unit S to unit P in order to perform a real time PCR reaction using a disposable containing a PCR reaction mixture.

In another preferred instrument according to an embodiment of the present invention, the unit I comprises a pipetting robot. Several different pipetting robots are known, wherein it is possible to provide a pipetting robot capable of transferring only a single set of primers and probes at a time or capable of transferring a plurality of the sets. In case of a unit S capable of synthesizing a plurality of sets in parallel using microtiter plates, it is preferred to provide a pipetting robot capable to transfer the content of the entire microtiter plate simultaneously to another microtiter plate within the unit P. Pipetting robots or modules of pipetting robots are commercially available from TECAN.

In yet another preferred instrument according to another embodiment of the present invention, the unit I comprises a UV measurement device. Such a UV measurement device is suitable to perform a quality control measurement of the synthesized primers and probes prior to the subsequent PCR amplification based on determining the amount of synthesized oligonucleotides.

In principle, it is possible to perform such a UV measurement at least in two different ways. The first alternative comprises extracting a portion of the synthesis product to perform the UV measurement within a separate disposable, whereas the portion is discarded after the UV measurement.

In a second, preferred alternative embodiment, the UV measurement device is a flow-through UV measurement device. This embodiment of the UV measurement device has the advantage that no synthesis product is wasted, because the UV measurement is performed during the transfer of the synthesis product from one disposable to another.

In another preferred embodiment of the instrument, the unit I further comprises a storage means for storing a plurality of multi-cavity disposables, which are preferably microtiter plates. This interface unit I is capable of storing a plurality of multi-cavity disposables with synthesized oligonucleotides and therefore, oligonucleotides synthesized in unit S may be stored in unit I in order to perform the subsequent PCR in unit P at a later time point.

According to another embodiment, the unit I further comprises means for setting up at least a first PCR reaction mixture. Setting up a PCR reaction mixture comprises providing all reagents necessary in the right concentration to perform a PCR reaction in addition to primers and probes in cavities of a multi-cavity disposable.

In a more preferred embodiment of the instrument, the unit I further comprises a plurality of containments for liquids. The containments for liquids are containments for the reagents necessary to perform a PCR reaction in addition to primers and probes, as well as containments for waste liquid and containments for washing solutions.

In a more preferred embodiment of the instrument, the unit I comprises means for setting up multiple PCR reaction mixtures in a multi cavity disposable, preferably in a microtiter plate.

In another preferred embodiment of the instrument, the unit I further comprises a transport means for transporting the PCR reaction mixtures into unit P. One example of transport means within the present invention, is a robot which can be used to transfer a multi cavity disposable, preferably a microtiter plate with PCR mixtures from the interface unit I to unit P. The multi cavity disposable to be transferred from unit I to unit P may additionally already comprise primers, probes and the sample. Alternatively, certain or all of the additional ingredients may be added to the multi cavity disposable only after the transfer to unit P.

An alternative transport means according to the present invention is a pipetting robot, whereas the pipetting robot transfers the PCR reaction mixtures from a multi cavity disposable within unit I to another multi cavity disposable within unit P.

In still another preferred embodiment, the unit I further comprises a temperature control device, capable of controlling the temperature within the cavities of a multi-cavity disposable.

The Real Time PCR Thermocycler Unit P

The real time PCR thermocycler unit P comprises a detection means in order to analyze the amplification in real time. Preferably, the detection means is capable of detecting fluorescence from probes used for the PCR protocol. More preferably, in another embodiment of the instrument, the unit P comprises a CCD camera.

In one embodiment of the instrument, the unit P comprises means for subjecting a multi cavity disposable to a thermocycling protocol. The instrument is capable of performing a plurality of PCR reactions in parallel using a multi cavity disposable, preferably a microtiter plate. This requires that unit P be designed such that each of the cavities of the multi cavity disposable can be exposed to temperature cycles in order to enable a PCR amplification of samples within the cavities.

In order to enable a plurality of PCR amplifications in parallel using a multi cavity disposable, it is preferred that unit P according to an embodiment of the present invention comprises a thermocycler which is a block cycler. Such block cycler devices capable of performing a plurality of PCR amplification in parallel that are suitable for the present invention are known to someone skilled in the art. In principle, it is possible to use any kind of Real time PCR technology that is based on a thermoblock comprising a microtiter plate format. Examples known in the art which however do not limit the scope of the present invention are the Roche Applied LightCycer480 instrument (Roche Applied Science catalog No: 4640268001), and the Biorad iCycler (Biorad catalog No. 170-8740).

System

Throughout the disclosure the word "system" is introduced to emphasize that an instrument is used in conjunction with multiple necessary disposables in order to achieve the intended use of the present invention.

Thus, one embodiment of the present invention is a system comprising
    an instrument according to the present invention, and
    at least one solid support disposable which is capable of acting as a starting support for oligonucleotide synthesis.

The solid support material is preferably CPG-material in order to perform standard oligonucleotide synthesis methods known to someone skilled in the art.

A preferred system according to the present invention comprises
    an instrument according to the present invention, and
    a solid support disposable which comprises at least one column with a frit comprising CPG particles.

Another preferred system according to the present invention comprises
    an instrument according to the present invention, and
    a solid support disposable which is planar.

In this preferred embodiment of the system, a planar solid support is used to perform the oligonucleotide synthesis. Procedures to perform a plurality of oligonucleotide syntheses on a planar support in parallel in order to produce an oligonucleotide array are known to someone skilled in the art (e.g. U.S. Pat. No. 5,700,637).

Another preferred system according to the present invention comprises
- an instrument according to the present invention, and
- a plurality of multi-cavity disposables, which are preferably microtiter plates.

As mentioned before, one or more disposables are necessary to apply the instrument of this invention for its intended use, whereas the number and the design of the disposables is depending on the respective embodiment of the instrument as well as the desired process according to the present invention. Since it is preferred that several syntheses and subsequent analyses are performed in parallel, the disposables are preferably multi-cavity disposables such as microtiter plates or column arrays. Moreover, certain of the microtiter plates or column arrays may have a frit at the bottom of each well of the microtiter plates or at the outlet opening of each column of the column arrays, respectively.

Synthesis Methods

In another aspect, the present invention is directed to an alternative and improved method for oligonucleotide synthesis which is particularly suitable in the context of an integrated oligonucleotide synthesis and PCR instrument. Within the scope of the invention, a single oligonucleotide may be prepared according to the methods disclosed below. Preferably, however, any method disclosed below is suitable for parallel synthesis of multiple oligonucleotides. Most preferably, the syntheses are performed in reaction compartments which are designed to conform to the microtiter plate format.

For all the disclosed embodiments, a person skilled in the art will recognize that it is necessary to optimize the concentrations of the different solutions that are required in the different steps of the disclosed workflows.

In a first embodiment, oligonucleotide synthesis is performed in at least one column or an array of columns (without a photo-cleavable linker) according to standard methods known in the art. After addition of the last phosphoramidite moiety, which still carries a 5' protective Trityl group, Ammonia is added onto the column and drawn through the frit by means of low under pressure, whereby the oligonucleotide comprising a base labile linker is cleaved from the CPG, and transferred through the frit into another reaction compartment comprising a frit at its bottom. In case of an array of CPG filled synthesis columns, the respective frit comprising reaction compartments may be arrayed within a microtiter plate. After repeated addition of Ammonia, the plate is completely sealed and incubated for at least about 2 h at room temperature when using mild chemistries or 8 h at 55° C. when using standard chemistry. The protective groups at the internucleoside phosphate linkages and the nucleotide bases are released. Afterwards, the ammonia can be evaporated by standard means known in the art. The preferred mild chemistry uses tert-butylphenoxyacetyl protected synthesis building blocks.

In a first specific embodiment, the sample is then guided through the frit by means of moderate under pressure onto a solid phase extraction column (commercially available from Varian (TOP DNA Cartridge) or from Waters (Oasis HLB 96). During the purification process, the Trityl protective group is cleaved. The final elution is performed with an Acetonitril/Water 1.1 mixture or with a solution of triethylammoniumacetat in water/acetonitril. In order to remove the acetonitril and salts the solution is applied on a gel filtration device resulting in an aqueous solution of oligonucleotides. This solution is finally stabilized upon addition of Tris buffer so that it can be subjected to further processes. Gilar, M., Bouvier, E., S., P., Journal of Chromatography, A, 890(1) (2000) 167-177.

In an alternative specific embodiment, a Hapten moiety which is preferably a Biotin moiety had been introduced at the 5' end in such a way that the 5' end comprises a biotinylated Trityl. After evaporation of ammonia, moderate under pressure is applied and the oligonucleotide is guided through the frit into a coated vessel which may be within a microtiter plate. The vessel is coated with a moiety that is capable of binding the Hapten, which has been introduced during nucleotide synthesis. Preferably, the coated moiety is either Streptavidin in order to capture Biotin-modified oligonucleotides onto the surface of the reaction vessel. Afterwards, the vessel is washed appropriately in order to remove any compounds such as incompletely synthesized oligonucleotides which do not carry a 5' hapten. Subsequently, according to standard conditions known in the art, a mild acid solution such as an acetic acid solution is added, which cleaves the biotinylated trityl group such that the oligonucleotide is again released from the surface of the reaction vessel into solution. Subsequently, an appropriate storage buffer is added in order to stabilize the oligonucleotide solution.

Alternatively, a photocleavable biotin is added during oligonucleotide synthesis by using the corresponding commercially available phosphoramidite to the 5'end (U.S. Pat. No. 5,247,081) Capturing with streptavidin was performed as described above, but the photo cleavage could directly be performed in the storage buffer.

In a second embodiment, at least one column or multiple columns, or an array of multiple columns are provided characterized in that each column contains CPG material positioned above a frit. A reactive group of the CPG, which is preferably a protected hydroxyl group, may already be connected to the CPG itself via a photo-cleavable linker. Alternatively, the hydroxyl group of a CPG may be reacted with a Phosphoramidate in a first synthesis step within the column, characterized in that the Phosphoramidate confers a photocleavable linker moiety and a protected hydroxyl group for subsequent oligonucleotide synthesis. Such photocleavable linker moieties and CPGs are well known in the art. McMinn, Dustin L., Hirsch, Robert, Greenberg, Marc, M., Tetrahedron Letters 39(24) (1998) 4155-4158; Anderson, Emma, Brown, Tom, Picken, Douglas, Nucleosides, Nucleotides & Nucleic Acids 22(5-8) (2003) 1403-1406; U.S. Pat. No. 5,258,506; WO 2007/082713.

Subsequently, oligonucleotide synthesis is performed according to standard method known in the art. Briefly, a reactive hydroxyl group, on which a chain extension in the 3'-5' direction can occur, is formed after removing the DMT protective group by acid treatment. Then 3' phosphoramidite derivatives of (deoxy) ribonucleosides that are also provided with a DMT protective group are successively coupled at the 5' end to each reactive group free of the DMT protective group in the presence of tetrazole. An intermediate containing a trivalent phosphorus atom comprising a beta-cyanoethyl, methyl, allyl or silyl protected hydroxyl group is formed, which is subsequently oxidized with iodine/H20/THF/pyridine.

After completion of the oligonucleotide chain, the protective groups at the internucleoside phosphates and at the nucleobases are cleaved upon adding ammonia, which is drawn through the column by means of applying low under pressure. Subsequently, the cleaved protecting groups are removed from the column through the frit upon addition of Acetonitril, which also is drawn through the column by applying low under pressure. Then, the oligonucleotide is released from the CPG upon illumination with an appropriate light source which cleaves the photo-cleavable bonding within the linker connecting the CPG and the newly generated oligonucleotide. Afterwards, the released oligonucleotide is transferred in the storage plate which is preferably a 96 well microtiter plate by drawing buffer through the frit again by means of applying low under pressure. When photocleavage results in a 3' phosphorylated oligonucleotide the phosphate group is removed during PCR according to methods known in the art.

The different inventive embodiments presented above are also compatible with the preparation of labeled oligonucleotide probes in which a label is introduced into the oligonucleotide preferably at the 5' or 3' end according to a method known from the prior art. In the case of a 5' label at the 5' position of the ribose of the 5'-terminal nucleotide, the incorporation is carried out by conventional methods using a hapten labeled or dye-labeled phosphoramidite at the end of the oligonucleotide synthesis (Beaucage, S., L., Methods in Molecular Biology 20 (1993) 33-61, S. Agrawal Publishers). Labeling at the 3' end is carried out by using commercially available CPG as a reactive solid phase support which already contains a detectable label in addition to the tritylated hydroxyl group. After cleavage of the DMT protective group standard oligonucleotide synthesis can be started at the hydroxyl group which is now free.

In another embodiment for parallel oligonucleotide synthesis, the oligonucleotides are synthesized in situ on a microarray chip (U.S. Pat. No. 5,700,637) for example in a 96 array format. The synthesized oligonucleotides are connected to the array substrate via photo-cleavable linker. Subsequent to the in situ synthesis, the surface of the microarray containing the oligonucleotides is positioned upside down on a microtiter plate in such a way that the separated areas of the solid support are aligned with the cavities of the first multicavity disposable and each cavity is closed by one separated area. The cavities of the plate are completely filled with buffer with the consequence, that there is a direct physical contact between the oligonucleotides bound on the array surface and the buffer solution contained in the cavities. After illumination with an appropriate light source, the oligonucleotides are directly released into the buffer solutions of the cavities of the microtiter plate. Preferably, the illuminating light passes the substrate prior to cleaving the photocleavable linkers.

Another aspect of the present invention is a quality control of the oligonucleotide synthesis. In this context, there exist 3 different possibilities:

a) 5' Label

In case that during each oligonucleotide synthesis, a detectable label such as Biotin is introduced at the 5' terminal of the newly synthesized oligonucleotide, it is possible to determine analytically the yield of full-length oligonucleotides that have been generated. In the embodiment of capturing such oligonucleotides as disclosed above, such a quality control is inherently implemented.

b) UV Monitoring

Subsequent to the oligonucleotide synthesis and purification, each sample can be monitored for its UV absorption at 260 nm, in order to determine a respective extinction coefficient. In the art, the value of OD 260 is an indicator for the presence and quantity of a nucleic acid in the solution monitored. In this context, the present invention also provides a method, characterized in that the UV absorbance of the synthesized primers is monitored in order to prove the quality of oligonucleotide synthesis and to determine the yield of the synthesis process. Preferably monitoring is performed in a flow through cuvette.

c) Test Oligonucleotide Syntheses

Alternatively, if oligonucleotide synthesis is performed in an arrayed format, it is possible to perform several oligonucleotide test syntheses at some of the array positions, more or less equally scattered on the array. The generated oligonucleotides can then be tested functionally for their ability to act as primers in a subsequent predefined PCR amplification reaction. Thus, the present invention also includes a method wherein multiple oligonucleotide test syntheses at positions equally scattered on the array are performed and the generated test oligonucleotides are subsequently tested functionally for their ability to act as primers in a predefined PCR amplification reaction.

Analytical Methods

In yet another aspect, a method of performing a real time PCR is disclosed and which comprises (i) performing an oligonucleotide synthesis of a first primer and a second primer in an integrated instrument, (ii) adding into a reaction vessel located in the integrated instrument
the nucleic acids sample that shall become analyzed,
the first and second primer,
adding all other reagent necessary for amplification and detection of a target nucleic acid, and (iii) amplifying and simultaneously monitoring amplification of the target DNA.

In order to perform all theses steps, the system requires a user programmable computer system which is capable of controlling the units S, I and P through a central processing unit.

There exist three different possibilities which are not mutually exclusive to each other.

In a first, simple embodiment, the user enters into the system the following information (i) the nucleic acid sequences of the amplification primers and, if required, the nucleic acid sequences of the detection probes, (ii) the modifications and labels of the oligonucleotides as required, and (iii) the thermocycling protocol for unit P.

In a second embodiment, the user enters one or more target sequences which shall become amplified without specifying the exact primer and probe sequences. The computer system comprises a software which is capable of designing an appropriate PCR assay and thus itself calculates all required primer and probe sequences as well as a suitable thermocycling protocol. Such software modules are already available and known by persons skilled in the art.

In a third embodiment, the computer system either itself comprises a database with genome sequence information or is linked to external sources comprising databases with genomic sequence information. The user enters a name or other specifier for a specific gene, the sequence of which shall become amplified and detected. The computer system comprises a software which is capable of identifying an appropriate target region suitable for PCR amplification from the databases, designs an appropriate assay and calculates all required primer and probe sequences as well as a suitable thermocycling protocol. Furthermore, based on the predetermined UV extinction coefficient determined for each oligonucleotide as disclosed above, the amount of all required primers and probes is adjusted.

In a further specific embodiment, the user may even only specify a specific virus or organism that shall become detected. The computer system is capable to select even an appropriate gene from the genomic databases, the detection of which by means of real time PCR is indicative for the presence of the virus or organism.

Furthermore, it is also within the scope of the present invention, if the programming of the synthesis unit S, the interface unit I and the real time PCR thermocycler unit P are at least partially uncoupled. For example, a primer and probe synthesis within synthesis unit S may be performed and the products may be stored in the interface unit I, prior to the programming of unit P. Amplification can then be programmed for a later time point. It is also possible to program the system in such a way that multiple amplification protocols are performed sequentially with the same batches of synthesized oligonucleotides that are intermediately stored within the interface unit I.

Monitoring amplification of the target DNA can be performed with various detection formats which are known in the art:

a) DNA Binding Dye Format

Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like SybrGreen I or SybrGold, for example, do not affect the efficiency of the PCR reaction. In this case, the SybrGreen is added to the sample together with all other reagents necessary for amplification of the target nucleic acid.

All other formats known in the art require the design of a fluorescent labeled Hybridization Probe which only emits fluorescence upon binding to its target nucleic acid. For all of these case, not only the amplification primers but also all fluorescently labeled hybridization probes are synthesized within the oligonucleotide synthesizer unit S according to any one of the inventive methods as disclosed above.

b) TaqMan Probe

A TaqMan probe is a single-stranded Hybridization Probe labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured (U.S. Pat. No. 5,538,848).

c) Molecular Beacons

These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

d) FRET Hybridization Probes

The FRET Hybridization Probe test format is especially useful for all kinds of homogenous hybridization assays (Matthews, J., A., and Kricka, L., J., Anal. Biochem. 169 (1988) 1-25. It is characterized by a pair of two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer, such that a fluorescence emission of the second component can be measured when both hybridization probes bind to adjacent positions of the target molecule to be detected.

When annealed to the target sequence, the hybridization probes must sit very close to each other, in a head to tail arrangement. Usually, the gap between the labeled 3' end of the first probe and the labeled 5' end or the second probe is as small as possible, i.e. 1-5 bases. This allows for a close vicinity of the FRET donor compound and the FRET acceptor compound, which is typically 10-100 Å.

Alternatively, to monitoring the increase in fluorescence of the FRET acceptor component, it is also possible to monitor fluorescence decrease of the FRET donor component as a quantitative measurement of hybridization event.

In particular, the FRET Hybridization Probe format may be used in real time PCR, in order to detect the amplified target DNA. Among all detection formats known in the art of real time PCR, the FRET-Hybridization Probe format has been proven to be highly sensitive, exact and reliable (WO 97/46707; WO 97/46712; WO 97/46714). Yet, the design of appropriate FRET Hybridization Probe sequences may sometimes be limited by the special characteristics of the target nucleic acid sequence to be detected.

As an alternative to the usage of two FRET hybridization probes, it is also possible to use a fluorescent-labeled primer and only one labeled oligonucleotide probe (Bernard, P. S., et al., Anal. Biochem. 255 (1998) 101-107). In this regard, it may be chosen arbitrarily, whether the primer is labeled with the FRET donor or the FRET acceptor compound.

At the end of the different oligonucleotide synthesis procedures according to the present invention, the different primers and also any kind of probes synthesized are usually placed in a multi cavity disposable such as e.g. a microtiter or picotiter plate. The disposable itself is preferably placed in an appropriate holding means. Such a holding means may be temperature controlled. For example, such a holding means may be a cooling block such that the primer and probe solutions may be stored at e.g. 4° C.

As a consequence, the primers and eventually the probes may then be stored without any loss of quality for at least 24 hours or even a week up to one month, before the PCR reaction mixture is prepared and the amplification and detection reaction is performed.

Furthermore, the generated primers and probes may be used for multiple PCR reactions that are performed subsequently in different multi cavity disposables. In other words, the present invention also provides a method characterized in that the synthesis step (i) is performed exactly once and steps (ii) and (iii) are performed multiple times in different multi cavity disposables.

In a further aspect of the present invention, it is possible to synthesize two different primers on the same CPG solid support or the same spot of an arrayed planar solid support. This requires that each primer be synthesized with a different set of Phosphoramidites, whereas each set has a different 5' OH protective group. For this embodiment, different strategies can be applied. Either by using a combination of a pair of Phosphoramidite sets with orthogonal transient protective groups e.g. photocleavable at different wavelengths, or by using a 1:1 mixture of CPG wherein one is protected with acid labile trityl and the other with a photocleavable protecting group. Alternatively, the tandem method with a cleavable linker between two oligonucleotides can be used (Pon, Richard, T., Yu, Shuyuan, Nucleic Acids Research 33(6) (2005) 1940-1948).

As a consequence, the step of preparing the PCR reaction mixture is facilitated, because only the sample containing the target nucleic acid and the other reagents required to perform the PCR amplification and detection reaction need to be added to generate a complete reaction mixture. Such an embodiment is particularly suitable for high throughput analyses with the same type of primers used in conjunction with a dsDNA binding dye such as SybrGreen.

Example

The design of an instrument according to the present invention is represented by the construction drawings of FIGS. 1-4. As it can be seen in FIG. 1, the synthesizer unit S comprises a housing 21 in which the oligonucleotide synthesis takes place, waste bottles 2 and a tray 1 with is designed to hold a microtiter plate that carries the newly synthesized oligonucleotides.

Figure 1:
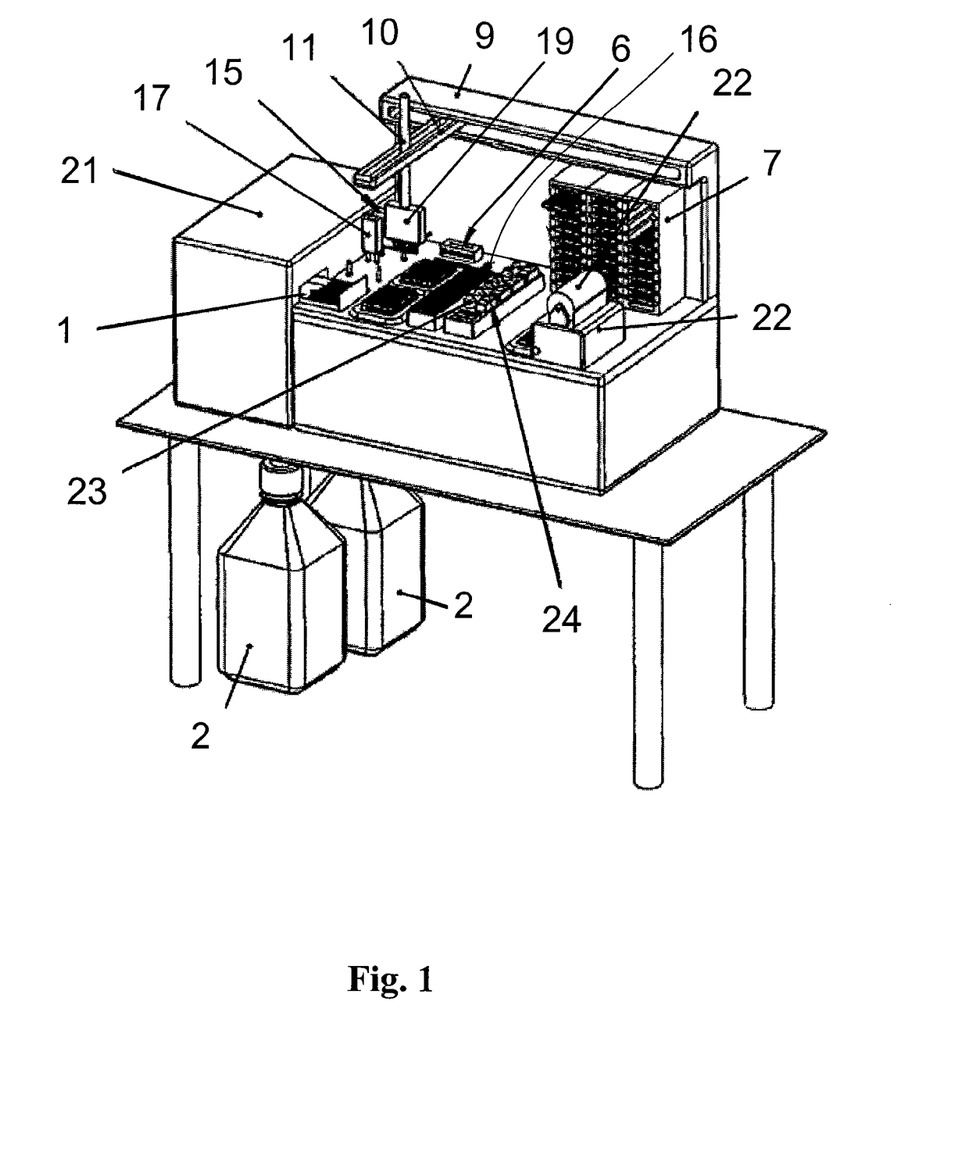
FIG. 1 is a schematic picture of one embodiment of the integrated instrument according to the present invention.
Figure 2:
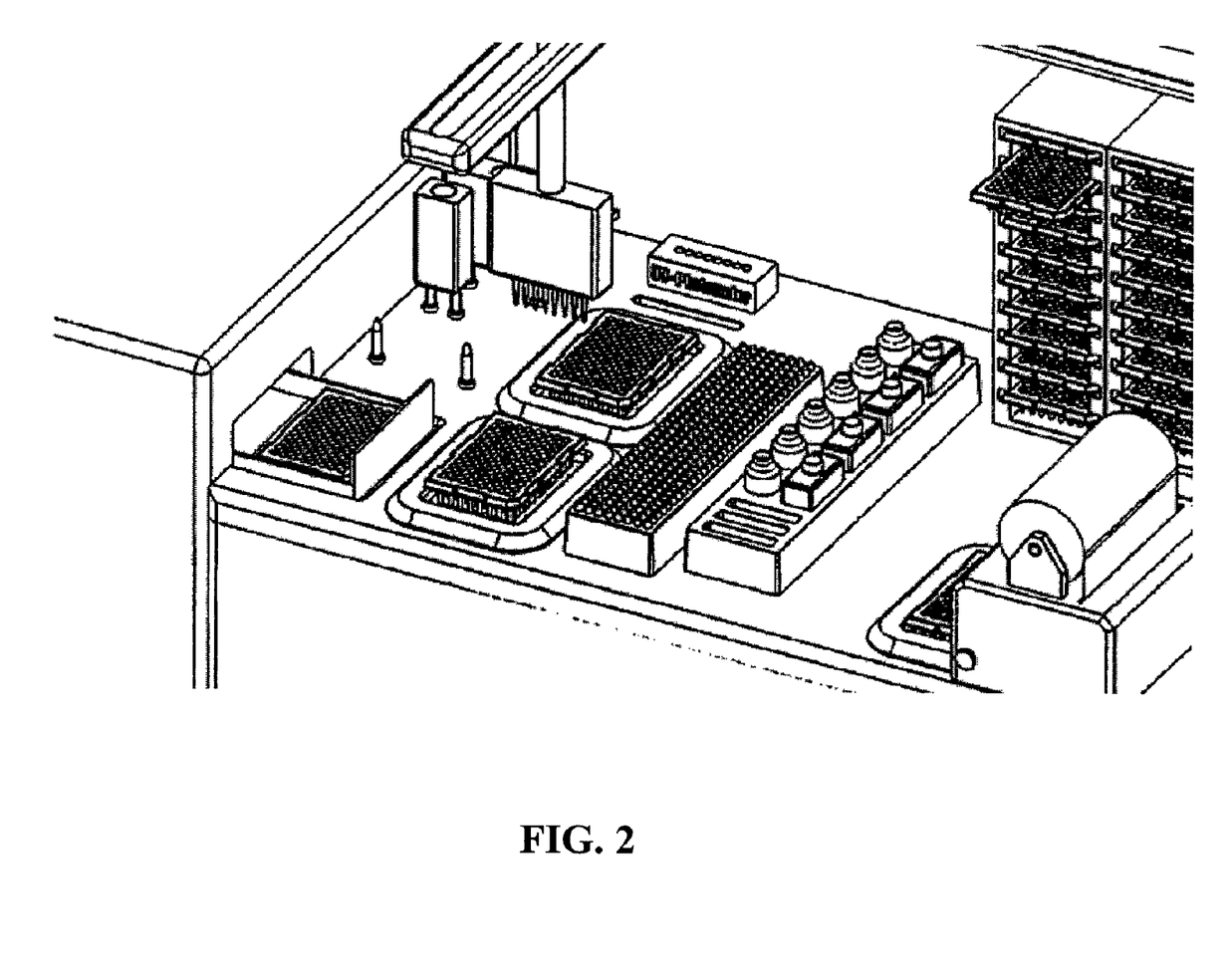
FIG. 2 is a schematic picture showing details of one embodiment of the integrated instrument according to the present invention.
Figure 3:
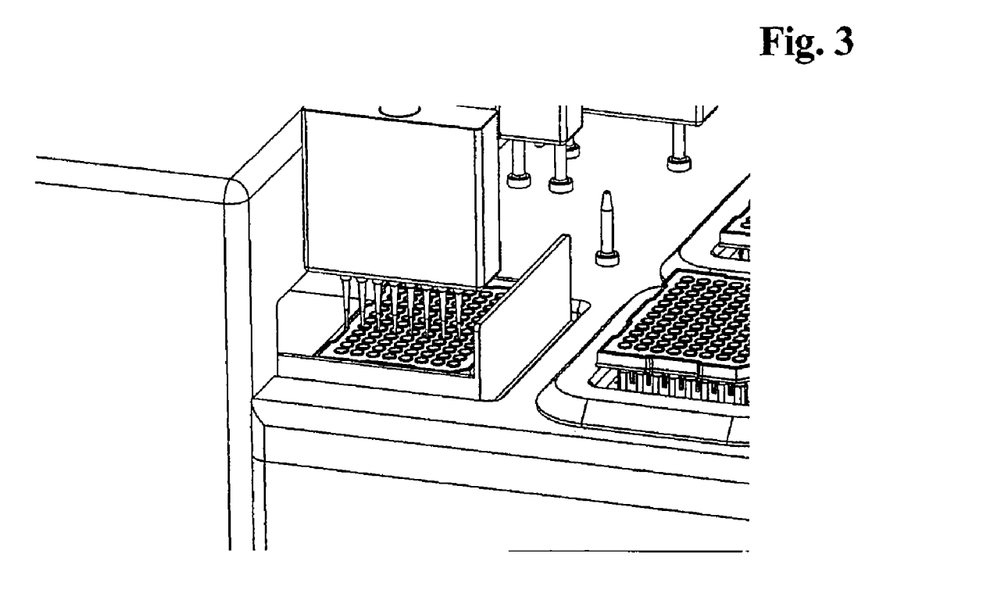
FIG. 3 is a schematic picture of a 8-time pipetting head useable with a pipetting robot according to the present invention.
Figure 4:
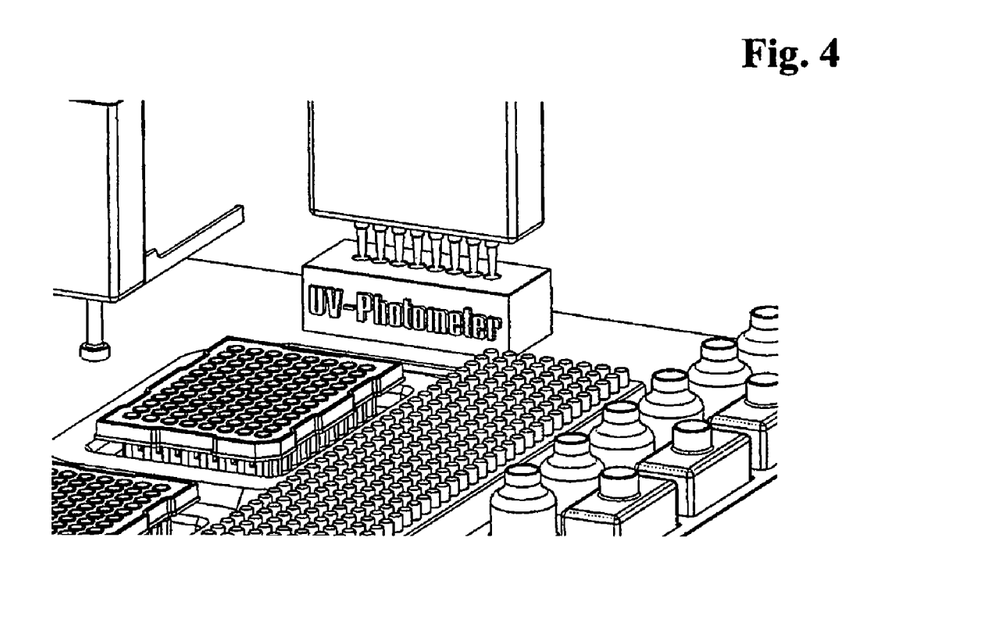
FIG. 4 is a schematic picture of a 8-time UV-measurement device according to the present invention.

The interface unit I comprises a pipetting robot 9, 10, 11, with a grip arm 17 for moving microtiter plates into various positions, and a pipetting head 19 for performing 8 pipetting steps in parallel. The Unit I further comprises a UV photometer 6, means for storing pipette tips 16, a tray 24 for holding bottles 23 comprising amplification reagents, a module 22 for sealing microtiter plates, and storage means 7 for storing a plurality of multi-cavity microtiter plates.

The thermocycler unit P is located within the box that is place in the middle of the table. It comprises two positions for microtiter plates located between tray 1 and the means for storing pipette tips 16. The two positions can be heated independently from each other. Thus, if a PCR reaction protocol is performed in one place, the other microtiter plate located in the other position can be filled with reagents for setting upon amplification reaction.

What is claimed is:

1. An integrated instrument for performing de novo synthesis of a plurality of oligonucleotides and real time PCR amplification of a target nucleic acid, said integrated instrument comprising:
   an oligonucleotide synthesizer unit for performing de novo synthesis of a plurality of oligonucleotides;
   a real time PCR thermocycler unit for performing amplification of a target nucleic acid;
   an interface unit operatively linking said synthesizer unit and said thermocycler unit; and
   a central processing unit which controls said synthesizer unit, said thermocycler unit, and said interface unit, such that subsequent to de novo synthesis of said plurality of oligonucleotides said interface unit automatically transfers a plurality of said oligonucleotides to said thermocycler unit, whereby said thermocycler unit automatically performs said amplification of said target nucleic acid with said plurality of said oligonucleotides.

2. The instrument according to claim 1, wherein said interface unit comprises a pipetting robot.

3. The instrument according to claim 1, wherein said interface unit comprises a UV measurement device.

4. The instrument according to claim 3, wherein said UV measurement device performs a quality control measurement of said at least one of primers and probes prior to said amplification of said target DNA.

5. The instrument according to claim 1, wherein said interface unit further comprises a storage means for storing a plurality of multi-cavity disposables, which are microtiter plates or picotiter plates.

6. The instrument according to claim 1, wherein said interface unit comprises means for preparing at least a first PCR reaction mixture.

7. The instrument according to claim 6, wherein said interface unit further comprises a transport means for transporting said PCR reaction mixtures into said thermocycler unit.

8. A method of performing a real time PCR comprising:
   (i) performing an oligonucleotide synthesis of a first primer and a second primer in an integrated instrument according to claim 1;
   (ii) adding into a reaction vessel located in said integrated instrument
      a) the target nucleic acids sample to be analyzed,
      b) said first and second primer synthesized in step (i), said first and said second primers being added into the reaction vessel by the interface unit and
      c) all other reagents necessary for a real time PCR of said target nucleic acid; and
   (iii) amplifying and simultaneously monitoring amplification of the target DNA in said integrated instrument.

9. The instrument according to claim 1, wherein said synthesizer unit comprises means for holding at least one CPG column or an array of CPG columns, said array of CPG columns being in a microtiter plate format.

10. The instrument according to claim 9, wherein said interface unit comprises a pipetting robot.

11. The instrument according to claim 10, wherein said interface unit comprises a UV measurement device.

12. The instrument according to claim 11, wherein said interface unit further comprises a storage means for storing a plurality of multi-cavity disposables, which are microtiter plates or picotiter plates.

13. The instrument according to claim 12, wherein said interface unit comprises means for preparing at least a first PCR reaction mixture.

14. The instrument according to claim 13, wherein said interface unit further comprises a transport means for transporting said PCR reaction mixtures into said thermocycler unit.

15. The instrument according to claim 9, wherein said synthesizer unit further comprises a suction device connected to said microtiter plate format, wherein said suction device draws said oligonucleotides into a cavity of a disposable in said synthesizer unit.

16. The instrument according to claim 1, wherein said synthesizer unit further comprises a housing in which said de novo synthesis of said oligonucleotides is performed.

17. An integrated system for automated oligonucleotide synthesis and subsequent real time PCR of a target nucleic acid, comprising:
   an oligonucleotide synthesizer unit including a solid support, a frit, suction means, a collection support, and a collection support closure means, the synthesizer unit adapted for de novo synthesis of a plurality of oligonucleotides utilizable in a real time PCR reaction;
   a real time PCR unit including a thermocycler component, a detection component, and a plurality of sample cavities, the real time PCR unit adapted for performing a real time PCR reaction with a plurality of sample;
   an interface unit including a pipetting robot and a flow-through UV measurement device, the interface unit mechanically linking the synthesizer unit and the real time PCR unit such that a plurality of the oligonucleotides synthesized by the synthesizer are automatically transferred from the synthesizer unit directly to the real time PCR unit for utilization in a real time PCR reaction; and a central processing unit adapted for receiving and executing a plurality of computer readable instructions from a non-transient machine readable media, the central processing unit operatively linking the synthesizer unit, the real time PCR unit and the interface unit such that upon initiation of the plurality of computer readable instructions the synthesizer unit performs de novo synthesis of a plurality of oligonucleotides, the interface unit automatically transfers a plurality of the synthesized oligonucleotides to the real time PCR unit and the real time PCR unit automatically performs a real time PCR reaction of a plurality of sample.

18. The integrated system of claim 17, wherein the solid support comprises a microtiter plate having a plurality of reaction cavities, each of the plurality of reaction cavities having a bottom portion, a frit being disposed at each of the bottom portions.

19. The integrated system of claim 18, wherein the frit disposed at each of the bottom portions separates each reaction cavity from the collection support.

* * * * *